United States Patent
Gaston et al.

(10) Patent No.: US 7,901,534 B2
(45) Date of Patent: Mar. 8, 2011

(54) METHOD OF MAKING DIAPERS WITH SUBSTANTIALLY REDUCED PRODUCTION OF DISCARDED WASTE MATERIAL

(75) Inventors: William W. Gaston, Greenville, NC (US); Michael G. Brosie, Greenville, NC (US)

(73) Assignee: Attends Healthcare Products, Inc., Greenville, NC (US)

( * ) Notice: Subject to any disclaimer, the term of this patent is extended or adjusted under 35 U.S.C. 154(b) by 34 days.

(21) Appl. No.: 12/284,774

(22) Filed: Sep. 25, 2008

(65) Prior Publication Data

US 2010/0071843 A1 Mar. 25, 2010

(51) Int. Cl.
B32B 37/00 (2006.01)
(52) U.S. Cl. ......... 156/256; 156/264; 156/265; 156/269; 156/270; 156/271; 604/385.23; 604/385.01
(58) Field of Classification Search ............. 604/385.01; 156/265, 271, 264
See application file for complete search history.

(56) References Cited

U.S. PATENT DOCUMENTS

| | | | | |
|---|---|---|---|---|
| 4,226,238 A | 10/1980 | Bianco | | 128/287 |
| 4,572,043 A | 2/1986 | Bianco | | 83/18 |
| 4,673,136 A | 6/1987 | Bianco et al. | | 241/280 |
| 4,806,303 A | 2/1989 | Binco et al. | | 264/5.04 |
| 5,725,714 A | 3/1998 | Fujioka et al. | | |
| 6,195,850 B1 * | 3/2001 | Melbye et al. | | 24/304 |
| 6,461,344 B1 * | 10/2002 | Widlund et al. | | 604/390 |
| 6,514,233 B1 | 2/2003 | Glaug | | |
| 6,913,718 B2 * | 7/2005 | Ducker et al. | | 264/37.1 |
| 6,994,761 B2 | 2/2006 | Klemp et al. | | 156/73.3 |
| 2004/0044325 A1 * | 3/2004 | Corneliusson | | 604/391 |
| 2004/0073188 A1 | 4/2004 | Mitsui et al. | | 604/391 |
| 2005/0059950 A1 | 3/2005 | Murguly | | 604/387 |
| 2006/0108054 A1 | 5/2006 | Ukegawa | | 156/160 |
| 2007/0289697 A1 | 12/2007 | Een et al. | | 156/164 |
| 2009/0084497 A1 | 4/2009 | Hornung et al. | | |

FOREIGN PATENT DOCUMENTS

| | | |
|---|---|---|
| DE | 10 2005 048 868 A1 | 4/2007 |
| EP | 0 768 073 A1 | 4/1997 |
| WO | 97/47265 | 12/1997 |
| WO | 02/24131 A1 | 3/2002 |

OTHER PUBLICATIONS

European Search Report.

* cited by examiner

*Primary Examiner* — Khanh Nguyen
*Assistant Examiner* — Margaret Squalls
(74) *Attorney, Agent, or Firm* — K&L Gates LLP

(57) ABSTRACT

Diapers are made with substantial reduction of waste using a composite web of diaper main body material having a liquid impervious outer layer, a liquid pervious inner layer and an absorbent intermediate layer there between. The composite web has an indeterminate longitudinal extent substantially intact and uncut with parallel lateral side edge margins for substantially the entire web length. An independent web of diaper tab material is cut into discrete tab sections of predetermined mating shapes with substantially no unused waste material. The tab sections are affixed to the opposite edge margins of, and at regular longitudinal spacings along, the composite web. The composite web is cut transversely at regular longitudinal intervals there along corresponding to the spacings of the tab sections to produce discrete diapers each having a generally rectangular main body and four tabs at the respective corners of the main body.

8 Claims, 6 Drawing Sheets

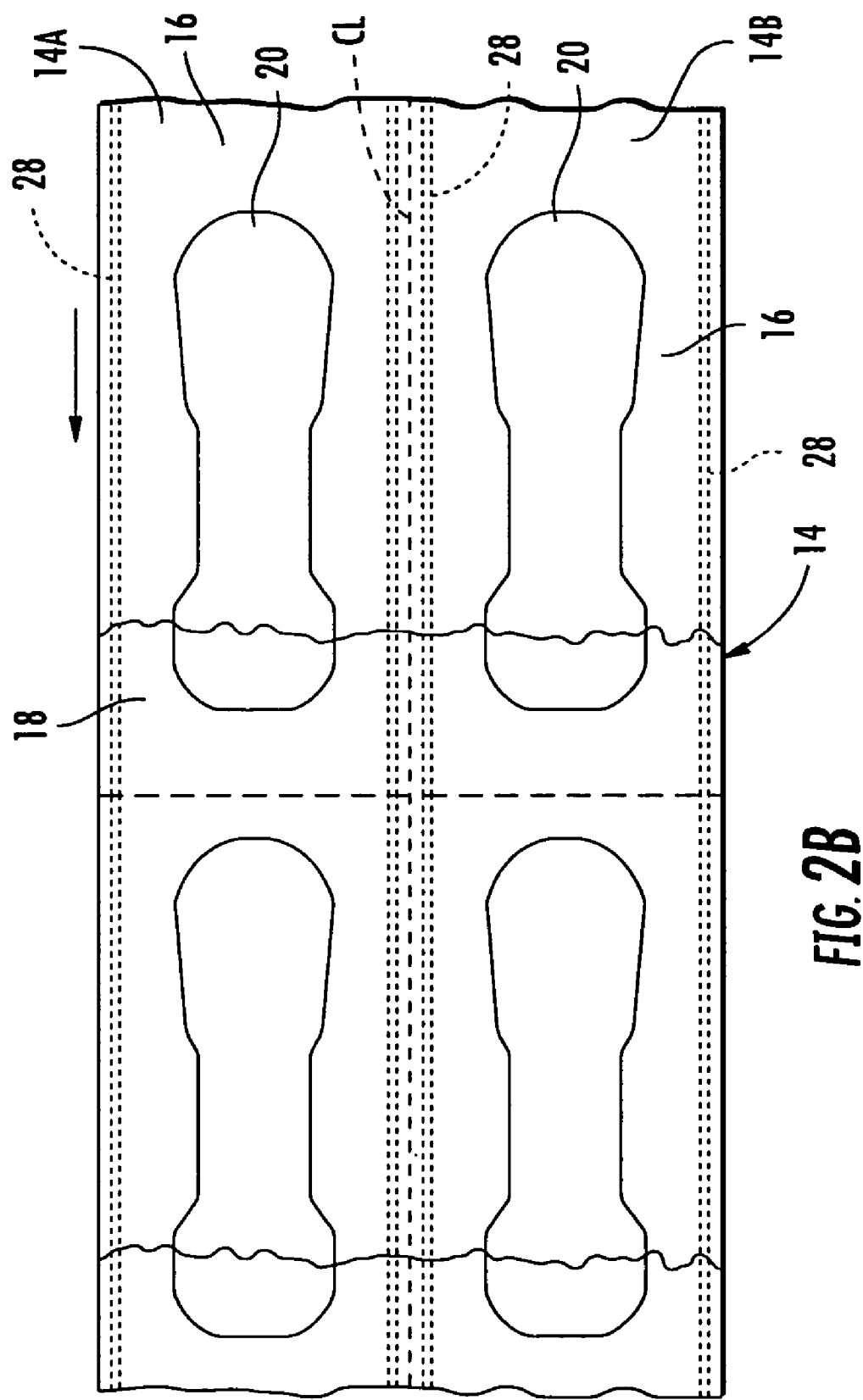

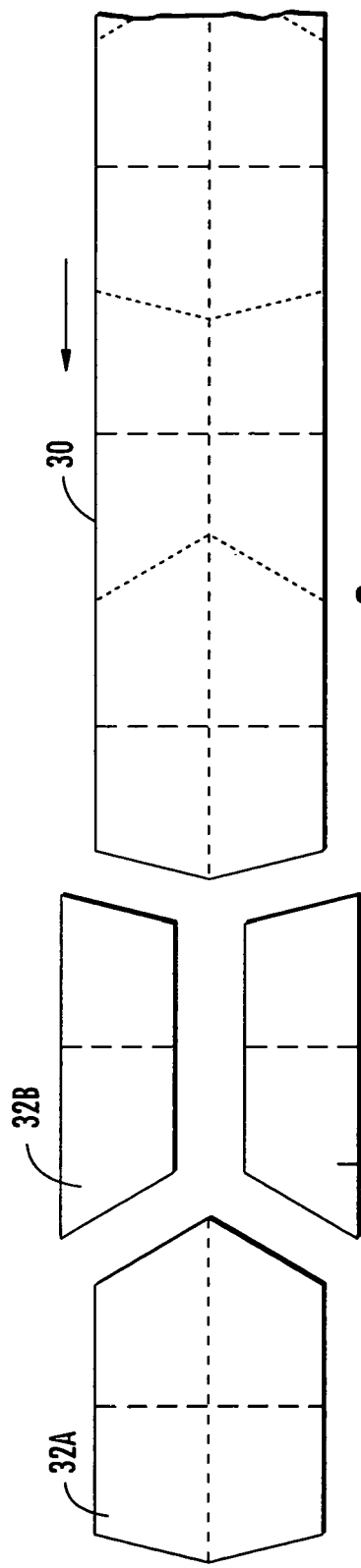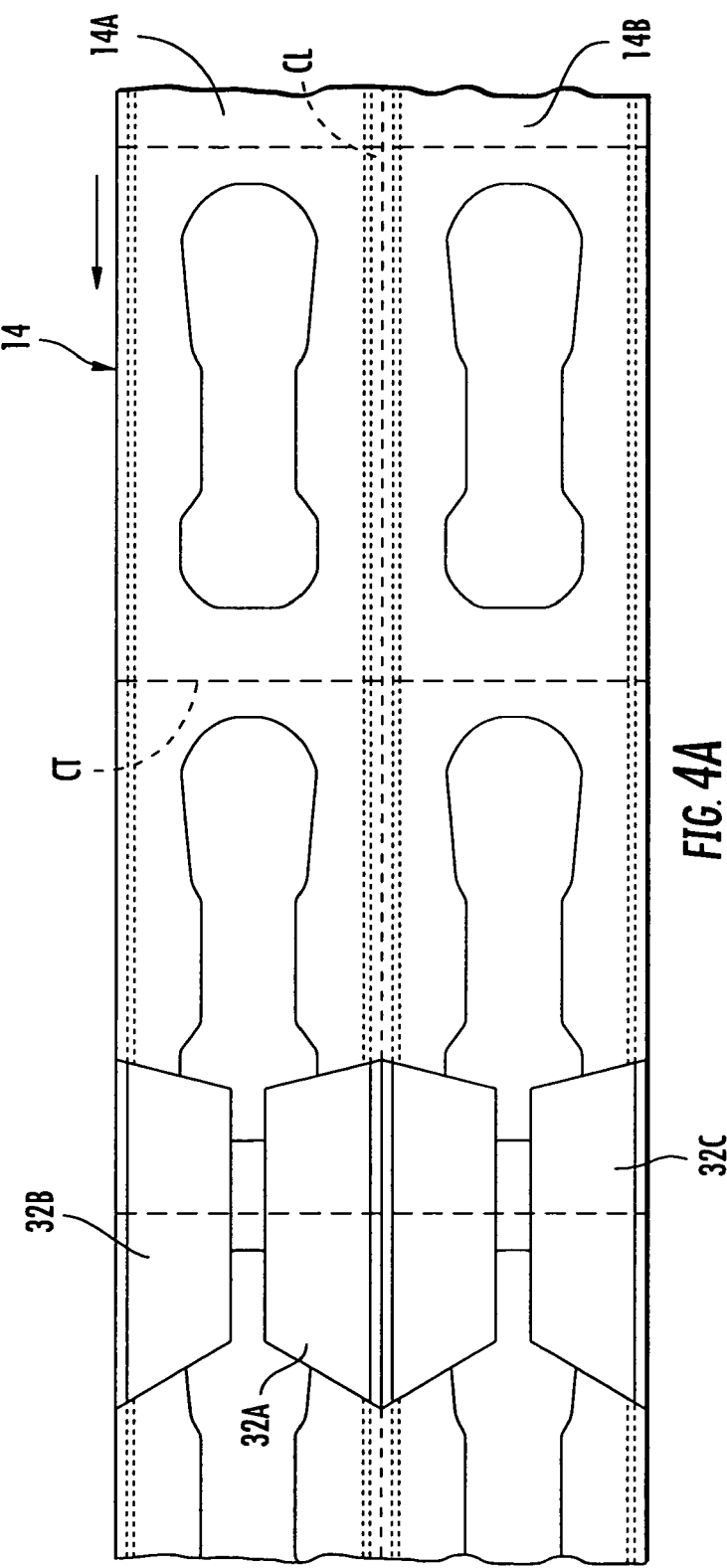

METHOD OF MAKING DIAPERS WITH SUBSTANTIALLY REDUCED PRODUCTION OF DISCARDED WASTE MATERIAL

BACKGROUND OF THE INVENTION

The present invention relates generally to the production of diapers, particularly disposable diapers, and more specifically, to methods of producing such diapers.

Over recent decades, disposable diapers have come to dominate the market for both infant diaper products and adult incontinence products, largely replacing traditional cloth fabric diapers and incontinent garments. Such disposable diapers, both for infants and adults, basically comprise three main components: an inner web or sheet of a liquid permeable material, typically a non-woven, for direct contact with the wearer's body, an intermediate core of a liquid absorbent material typically in the form of a pad of hydrophilic fibers and often including a supplementary absorbent medium such as a super absorbent polymeric material for capturing and holding bodily fluids passing through the permeable inner layer, and an outer web or sheet of a liquid impervious material usually comprised of a laminate of film and non-woven materials to retain liquid within the absorbent core against leakage from the diaper.

For optimal fitting of such diapers to the typical contours of a wearer's body, such diapers commonly are formed of an overall hourglass shape providing a narrowed crotch area situated between wider front and back portions respectfully for covering the abdomen and buttocks of a wearer. The laterally extending margins of the wider front and back portions of the diaper form wing-like tabs which can be overlapped with one another when worn so as to encircle fully the waist of the wearer and, together with the crotch portion, to form leg openings encircling the upper legs of the wearer adjacent the wearer's crotch. The wing-like tab portions are typically provided with fastener elements, such as adhesive elements, hook-and-loop fastener elements, or other appropriate means for securely holding the tab-portions in overlapping relationship. The diapers are also often provided with elastic bands or filaments within the lateral borders of the crotch portion to enhance conformance of the crotch portion to the body of the wearer and thereby additionally mitigate risk of fluid leakage.

The process of making diapers of the basic above-described construction is generally well known in the relevant art and is accomplished by a substantially fully automated process wherein respective webs of liquid impervious and liquid permeable sheet roll stock are fed simultaneously with a web of absorbent padding material through so-called converting machinery which orients the respective webs in a sandwich-like relationship to be assembled by an appropriate manner of bonding of the webs, e.g., by ultrasonic welding. Each respective web is typically of an elongate continuously length of material having parallel lateral side edges. In the process of feeding the web of the outer liquid impervious layer, appropriate segments of the material are severed from each opposite side of the moving sheet roll stock at regular intervals to form a repeating pattern of hourglass shapes along the length of the advancing web material. In some cases, the sheet roll stock of liquid permeable material for forming the inner web may be of a dimension laterally coextensive with that of the outer web of material, in which case corresponding segments of material are severed from the inner web also, but alternatively the inner web may be of a more narrow lateral dimension to only overlie the crotch portion and the corresponding central regions of the front and rear portions of the outer web.

Disadvantageously, all such materials severed from the outer web, and optionally also from the inner web, constitute waste which must be discarded and may comprise up to approximately 11 percent of the overall costs of materials utilized in diapers. Accordingly, there is a substantial recognized need within the industry for alternative methodologies or techniques in the fabrication of such diapers that will enable the creation of discarded waste material to be eliminated or at least significantly reduced.

SUMMARY OF THE INVENTION

It is accordingly a general object of the present invention to provide an improved method of making diapers, particularly disposable diapers, with substantially reduced production of discarded waste material. A more particular object of the present invention is to eliminate the necessity of severing and discarding segments of web material in order to form diapers in a traditional hourglass configuration. A further object of the present invention is to provide a methodology by which the output by a single diaper production line can be essentially doubled.

Briefly summarized, the present invention provides a method of making diapers wherein a composite web of material for making a diaper main body is provided with a substantially liquid impervious outer layer, a substantially liquid impervious inner layer, and an absorbent intermediate layer between the outer and inner layers. The composite web has a longitudinal extent of an indeterminate continuous length which is substantially intact and uncut without any portions or sections severed therefrom and discarded, such that the composite web has substantially parallel linear edge margins along opposite lateral sides thereof for substantially the entire continuously length of the composite web. An independent web of material for forming diaper tabs is also provided and has a longitudinal extent of indeterminate continuous length. The web of tab material is cut into discrete tab sections of predetermined mating shapes which produce substantially no waste material which is unused as the tab sections. The tab sections are affixed to the opposite edge margins of, and at predetermined regular longitudinal spacings along, the composite web. Thereafter, the composite web is cut transversely at regular longitudinal intervals along the web corresponding to the spacings of the tab sections, to produce a plurality of discrete diapers each having a generally rectangular main body formed by the material of the composite web and four tabs at respective corners of the main body, formed by the tab sections.

In a preferred embodiment of the method of the present invention, the composite web is preformed by providing the outer and inner layers of coextensive indeterminate continuous lengths having corresponding substantially parallel linear longitudinal edges along opposite lateral sides thereof, and assembling the outer and inner layers coextensively in overlying relation with one another substantially without cutting and discarding any material from the inner and outer layers. In assembling the outer and inner layers, the absorbent material is inserted therebetween, preferable as discrete absorbent pads spaced longitudinally from one another. The tab sections are preferably affixed to the composite web at the spacings intermediately of the absorbent pads.

The transverse cutting of the composite web is preferably performed at the spacings intermediately of the absorbent pads at a location longitudinally intermediately along the tab sections for separating each tab section into at least two tabs.

The tab sections may be affixed to the composite web in any suitable manner, but most preferably by means of a fin-type seal between each tab section and the composite web.

Most preferably, the steps of the present method are performed while continuously advancing the composite web of diaper main body material and the independent web of diaper tab material in synchronism with respect to each other.

In a preferred embodiment, the composite web is formed with the discrete absorbent pads arranged in two laterally spaced longitudinal rows of correspondingly longitudinally spaced absorbent pads inserted and assembled between the inner and outer layers of the composite web. The tab sections are affixed not only at the opposite edge margins of the composite web but also intermediate the longitudinal rows of the absorbent pads, with the tab sections at predetermined regular longitudinal spacings along the composite web corresponding to the spacings intermediately of the absorbent pads. The composite web is cut both transversely at regular longitudinal intervals at locations longitudinally intermediately along the tab sections and also cut longitudinally between the two rows of absorbent pads transversely intermediate the tab sections therebetween. In this manner, two identical pluralities of discrete diapers are produced, with each diaper having a generally rectangular main body formed of the composite web material and four tabs at the respective corners of the main body formed by the tab sections.

BRIEF DESCRIPTION OF THE DRAWINGS

FIG. 2B is a schematic depiction in top plan view corresponding to the illustration of the production of the composite web of FIG. 2A;

FIG. 3 is a schematic depiction of a web of diaper tab material being advanced and cut into discrete tab sections in accordance with a preferred embodiment of the method of the present invention;

FIGS. 4A and 4B schematically depict sequential steps in the placement and affixation of the diaper tab sections to the composite web, followed by the transverse and longitudinal cutting of the composite web to produce plural discrete diapers, also according to a preferred embodiment of the method of the present invention.

DETAILED DESCRIPTION OF THE PREFERRED EMBODIMENTS

Figure 1:
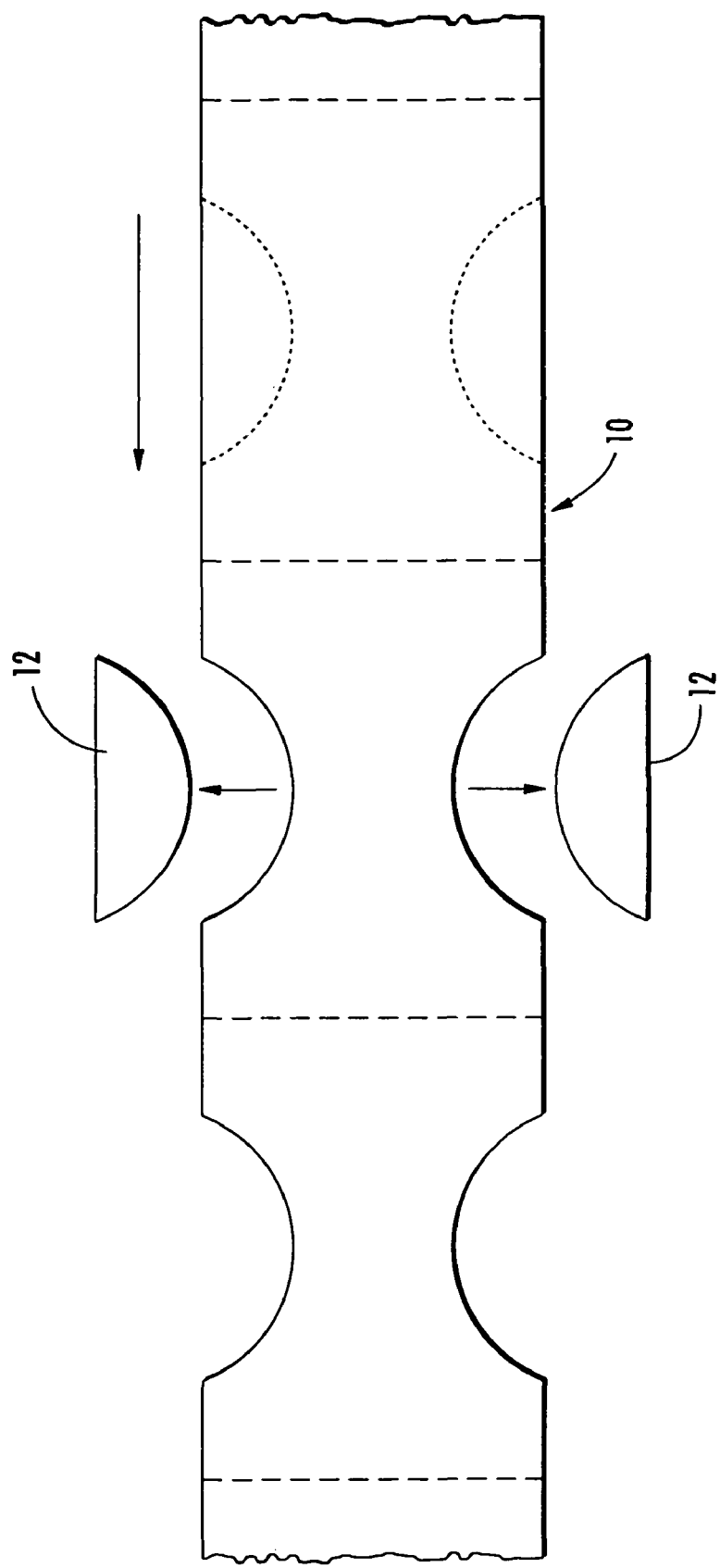
FIG. 1 is a schematic depiction of the conventional prior art methodology for fabricating disposable diapers in the traditional hourglass shape as above-described.

Referring now to the accompanying drawings FIG. 1 depicts in simplified schematic form the general methodology of the current state of the art for the mechanized automated manufacture of disposal diapers wherein an advancing web of diaper material, generally indicated at 10, is preliminarily cut to remove arcuate segments 12 from the opposed side edges of the web 10 at regular periodic spacings to pre-form the web into a repeating lengthwise series of hourglass shapes. This pre-forming step is performed on at least the web material 10 to be incorporated into a diaper as the liquid impervious outer layer of the diaper, but may also be performed for some diaper embodiments to correspondingly pre-form the web material for the liquid pervious inner layer (not shown). The arcuate segments 12 which are thusly removed constitute waste which is discarded. Even though such waste material may be susceptible of recycled use, the waste adds significantly to the costs of production of diapers, as already discussed above.

The present invention seeks to overcome these disadvantages of known diaper forming methods by a novel methodology depicted schematically in FIGS. 2A, 2B, 3, 4A and 4B. In basic generalized terms, the present invention contemplates the initial formation of a composite web of material suitable for use as the main body of a diaper, that is, comprising a liquid impervious outer layer, a liquid pervious inner layer and an absorbent intermediate layer therebetween as depicted schematically in FIGS. 2A and 2B; the coordinated formation of a separate independent web of material into discrete diaper attachment tab sections, as depicted schematically in FIG. 3; and the subsequent affixation of the diaper attachment tab sections to the composite web, as depicted schematically in FIG. 4A, followed by the cutting of the composite web into a plurality of discrete diapers, as depicted schematically in FIG. 4B.

Figure 2A:
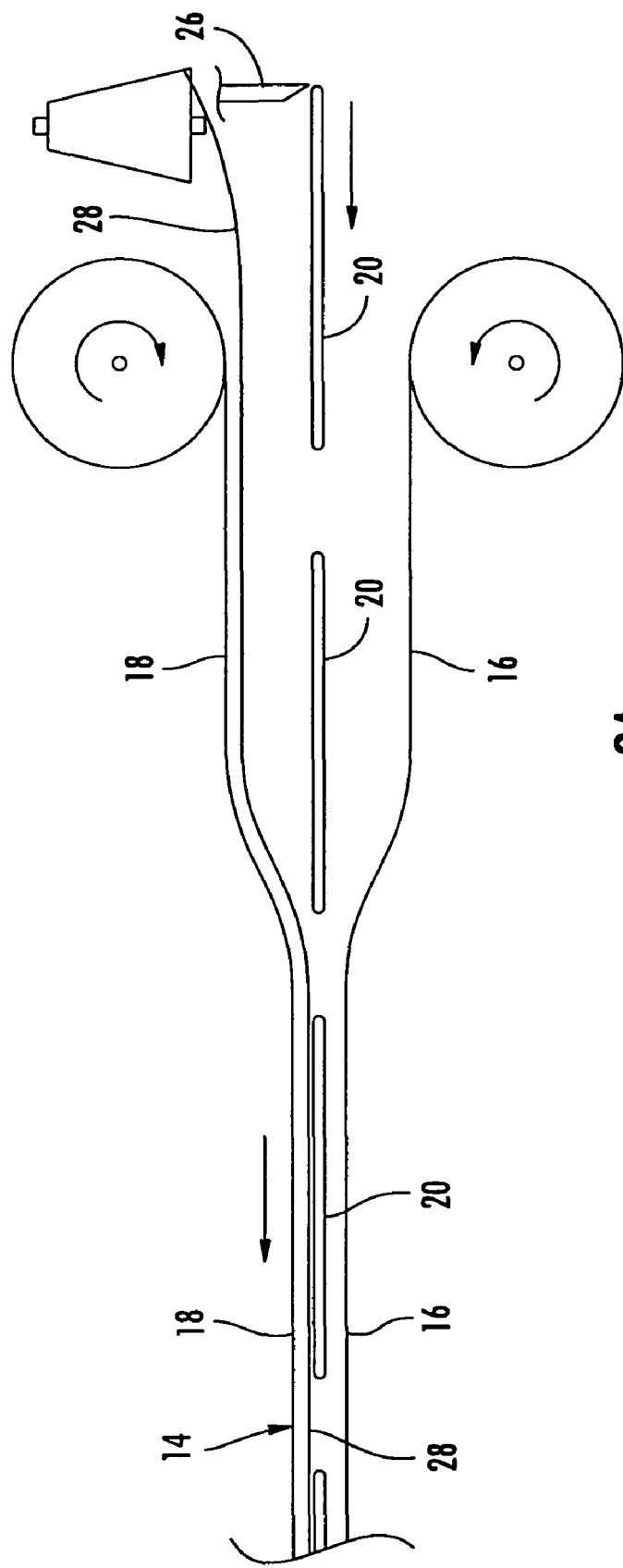
FIG. 2A is a schematic depiction in side elevation showing the formation of a composite web of material for a diaper main body in accordance with a preferred embodiment of the method of the present invention.

With reference more specifically to FIGS. 2A and 2B, the composite web is indicated in assembled form generally at 14 and basically comprises a web or sheet 16 of a liquid impervious material such as a thermoplastic film to serve as the outer layer (sometimes called the bottom layer) of the main body of a diaper. Commonly, the outer, or bottom, layer may include a non-woven web laminated to the thermoplastic film along a central area of the web. The composite web 14 further comprises a web or sheet 18 of a liquid permeable or liquid pervious material, such as a non-woven web suitable to form the inner, or top, layer of the main body of a diaper. Each web 16, 18 is of a flat open-width sheet-like configuration having substantially parallel linear longitudinal edges (see FIG. 2B) along opposite lateral sides thereof. The webs 16, 18 are stored on and fed from respective storage rolls 22, 24 on which an elongate continuous indeterminate length of the web is wound, with the webs being fed therefrom to advance in a common direction for assembly together in width wise and length wise coextensive overlying relation to one another.

As the outer and inner webs 16, 18 are thusly advanced, the absorbent core material is correspondingly advanced from a suitable source of supply to be fed between the outer and inner webs 16, 18, for assembly therewith as an intermediate absorbent layer. The absorbent material may be of any suitable type and form capable of liquid absorption, e.g., a non-woven web of padding material of hydrophilic fibers, and may incorporate supplementary absorptive media such as a super absorbent polymeric material impregnated in, intermingled with, or otherwise contained by the absorbent web. The absorbent web is preferably cut as it is advanced into discrete absorbent pads which are delivered between the outer and inner webs 16, 18, at lengthwise spacings from one another to form respective absorbent crotch pads in discrete diapers to be subsequently formed according to the present method. This technique is commonly known and used in the industry and therefore is only schematically represented in FIG. 2A by the discrete absorbent pads 20 advancing forwardly from a cutting element represented only by knife 26. In the cutting of the absorbent web into discrete absorbent pads 20, it is additionally preferred that the absorbent web be cut into an oblong hourglass configuration, as best shown in FIG. 2B, in conformity to the general shape of the crotch and adjacent forward and rearward areas in a diaper when worn. However, it is to be understood that the present invention is not limited to this type and configuration of absorbent pad. For example, the web of absorbent material could be fed as a continuous uninterrupted length of web correspondingly to that of the outer and inner webs 16, 18.

In the formation of the composite web 14, other common elements of disposable diapers may also preferably be incorporated into the web, such as elastic filaments 28 to extend along opposite side edges of the composite web. Other common components of disposable diapers not shown in the drawings may also be incorporated into the composite web at this stage of assembly, e.g., a perforated acquisition distribution film layer may desirably be fed and inserted between the absorbent pads 20 and the inner web layer 18. These and other common diaper construction elements are not excluded from use in the present invention but do not form a part of the novelty of the present invention.

As depicted in FIG. 2B, in a preferred embodiment of the present invention, the outer and inner webs 16, 18, together with the absorbent pads 20 and the elastic filaments 28 are assembled to form simultaneously two identical composite webs in side-by-side relationship, integrated together by the common outer and inner webs 16, 18. For such purpose, the absorbent pads 20 are delivered between the webs 16, 18 in side-by-side pairs to form the pads in the integrated composite web 14 in two laterally spaced longitudinal rows of pads which are correspondingly spaced longitudinally along the composite web 14. Likewise, the elastic filaments 28 are fed between the inner and outer webs 16, 18 simultaneously along the opposite outer lateral edge margins of the webs 16, 18 and also along opposite sides of the longitudinal centerline extending the length of the outer and inner webs 16, 18, (indicated at CL) between the spaced rows of absorbent pads 20, all as depicted in FIG. 2B. The two integrated composite webs are hereinafter respectively identified as composite webs 14A and 14B while the two composite webs 14A and 14B are collectively referred to herein as composite web 14. The respective components of the composite web 14 are joined together in any suitable known manner, such as the common technique of ultrasonic welding of the respective webs together, thereby capturing and retaining the absorbent pads 20 and the elastic filaments 28 between the outer and inner webs 16, 18.

FIG. 3 depicts schematically a processing line, operable in parallel and synchronism to the methodology for forming the composite web 14 depicted in FIGS. 2A and 2B, by which is provided the separate independent web of material for forming diaper attachment tabs. The attachment tab web is represented schematically at 30 and is basically an open-width flat web of material of any suitable composition compatible for affixation with the material of the outer web 16 of the composite web 14, e.g., by ultrasonic welding or another suitable means of affixation. For example, the diaper attachment tab web 30 may be made of the same thermoplastic film as is incorporated into the outer web 16, or may be a non-woven web having a stretchable panel or stretch properties. The widthwise dimension of the diaper attachment tab web 30 is preferably less than one-half of the overall lateral width of the composite web 14 such that the web 30 may be conveniently cut into discrete tab sections for attachment as tab portions to each of the side-by-side composite webs 14A and 14B, all as more fully described below.

The diaper attachment tab web 30 is of an elongate continuous indeterminate length having substantially parallel edges along its opposite outer lateral sides. The diaper attachment web 30, according to the methodology of the present invention, is continuously advanced and severed lengthwise and transversely in a repeating pattern of cuts producing three discrete tab sections 32A, 32B, 32C for each repeating pattern of cuts. As depicted in FIG. 3, the broken lines in the unsevered section of the web 30 represent the repeating pattern of cuts, with one grouping of severed tab sections 32A, 32B, 32C being shown as having advanced to the point in the processing line of being severed into the discrete tab sections.

As previously indicated, the advancing delivery of the diaper attachment tab web 30 is coordinated in synchronism with that of the production of the composite web 14 occurring in parallel. FIG. 4A depicts the affixation of the tab sections 32A, 32B, 32C to the advancing composite web 14. In FIG. 4A, the broken lines CT, which extend transversely across the composite web 14 in perpendicular relation to the longitudinal center line CL along the composite web 14 midway intermediate the spaced pairs of absorbent pads 20, represent cutting locations at which the composite web 14 will be subsequently severed into discrete individual diapers at a later downstream point in the diaper producing methodology, as more fully described hereinbelow. As will be seen, the tab section 32A is of a size and configuration suitable to be severed into four discrete diaper tabs, as represented by the broken lines depicted in tab section 32A. Similarly, each of tab sections 32B and 32C are of a size and configuration essentially one-half that of the tab section 32A, so that each tab section 32B and 32C is suitable to be severed into two discrete diaper tabs, as represented by the transverse broken lines depicted in such tab sections 32B and 32C.

Following severing of each repeating group of three tab sections 32A, 32B, 32C, the severed tab sections are transferred by suitable mechanical implements (not shown) as are known in the art, onto the surface of the inner web 18 at one transverse cutting location CT, as depicted in FIG. 4A. More specifically, the tab section 32A is rotated 180 degrees from its orientation when cut from the diaper attachment tab web 30 and, in such rotated orientation, is placed at the intersection of the longitudinal center line CL and the transverse cutting line CT in the composite web 14 so as to symmetrically overlap each of the adjacent four diaper sections of the composite webs 14A, 14B, whereby the tab cutting lines transversely and longitudinally in the tab section 32A coincide with the underlying transverse and center lines CT, CL in the composite web 14. Similarly and simultaneously, the two tab sections 32B and 32C are transferred to overlie laterally outward edge margins of the composite web 14 with their respective transverse cutting lines coinciding with the transverse cutting line CT across the composite web 14, whereby each tab section 32B and 32C respectively overlies symmetrically the two adjacent diaper sections of the respective composite webs 14A and 14B.

With the tab sections 32A, 32B and 32C thusly positioned overlying the composite web 14, the respective tab sections are affixed to the composite web 14, preferable by ultrasonic welding. More specifically, the laterally outwardly oriented edges of the tab sections 32B and 32C are bonded respectively to the underlying laterally outward edge margins of the respective composite webs 14A, 14B along lines just outwardly of the elastic filaments 28 which extend along such edge margins of the composite webs 14A, 14B, thereby forming a fin-type seal between the tab sections and the composite web. Simultaneously, the tab section 32A is bonded along its lengthwise extending central cutting line to each composite web 14A, 14B along the longitudinal center line CL of the composite web 14 laterally adjacent the elastic filaments 28 extending therealong, similarly forming a fin-type seal.

Figure 4B:
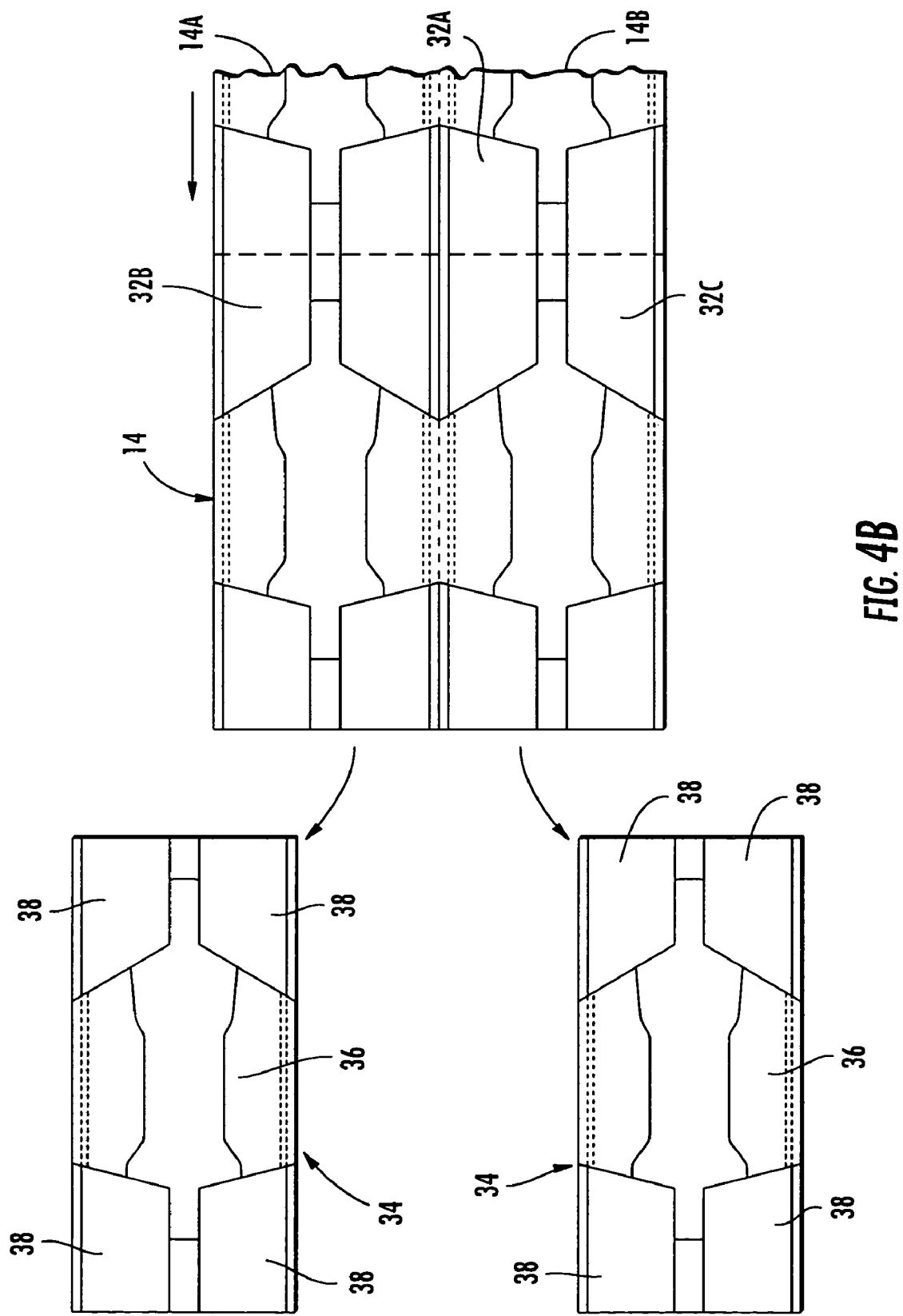

As the composite web 14 with the thusly attached diaper sections 32A, 32B and 32C is further advanced along the diaper producing line, the composite web 14 and the attached tab sections 32A, 32B and 32C are severed transversely at the cutting line CT and longitudinally along the center line CL, thereby severing the tab section 32A into four discrete diaper tabs and severing each of tab sections 32B and 32C into two discrete diaper tabs, and thereby producing two discrete diapers each with four diaper tabs, as represented by diapers 34 in FIG. 4B. As the composite web 14 continues to advance with subsequently attached diaper tab sections 32A, 32B and 32C at following transverse cutting lines CT, the repetitive performance of the methodology as above described thusly produces simultaneously two identical pluralities of diapers 34.

Figure 5:
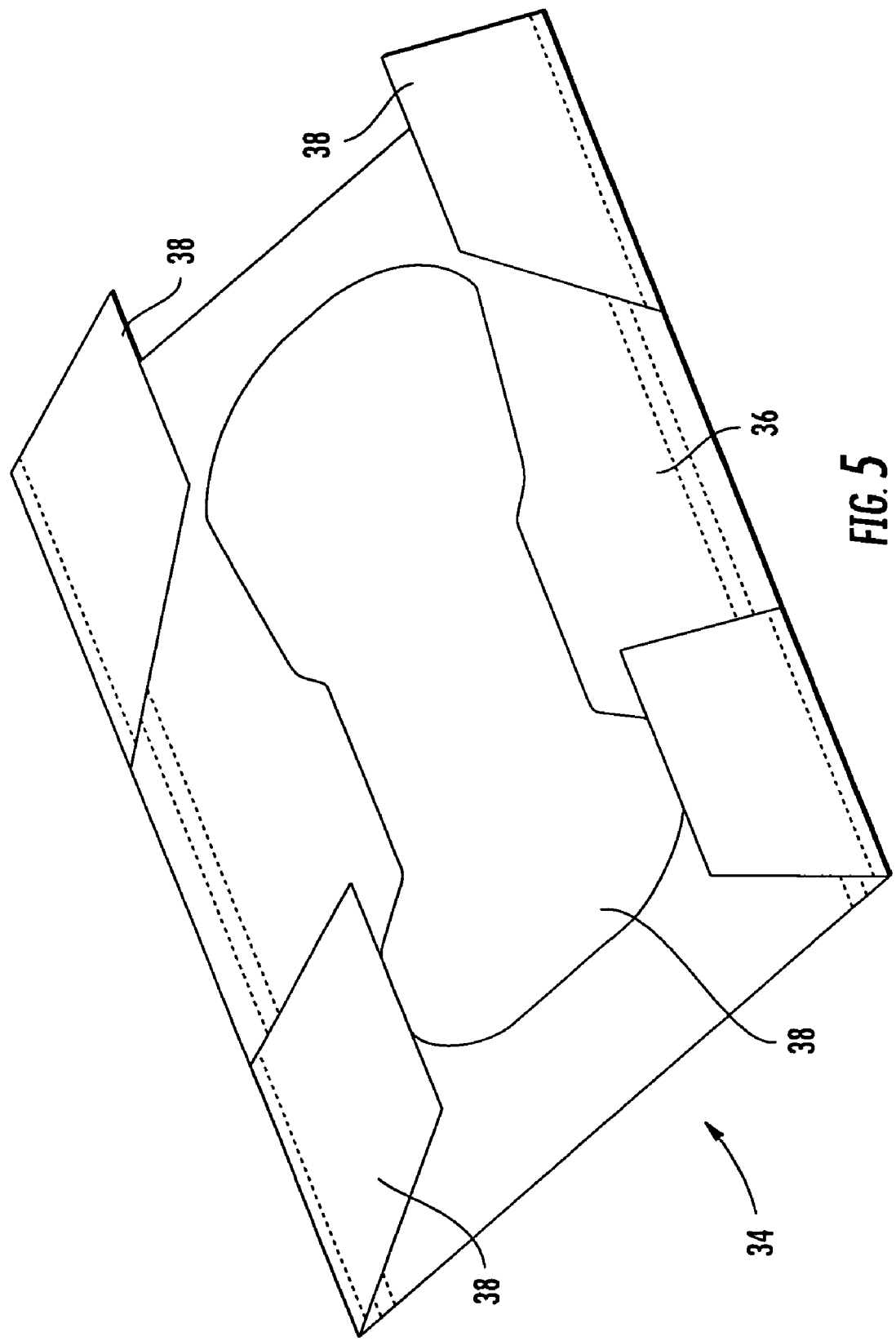
FIG. 5 is a schematic perspective view of a diaper made in accordance with the preferred embodiment of the method of the present invention depicted in FIGS. 2A, 2B, 3, 4A and 4B.

FIG. 5 depicts schematically the basic construction of each such diaper 34. As will be recognized, for sake of clarity, the diaper 34 in FIG. 5 is depicted with the elastic filaments 28 still stretched in the elongated state in which the filaments are held throughout the method steps depicted from FIGS. 2A and 2B through the final process steps of FIGS. 4A and 4B. However, those persons skilled in the art will recognize that, upon severing of the individual diapers 34, the elastic filaments 28 will be caused to relax longitudinally.

Each diaper 34 thusly has a main diaper body 36 essentially of a rectangular configuration as formed by one diaper section of one composite web 14A, 14B, comprising basically an outer layer of web material 16, an inner layer of web material 18, and a single absorbent pad 20 disposed therebetween, and with four individual diaper tabs 38 at the respective corners of the main diaper body 36 disposed in overlying relation to the main diaper body 36 by virtue of the fin-type seal by which the tabs 38 were bonded to the lateral edges of the main diaper body 36 in the process step of FIG. 4A.

The methodology of the present invention will thus be understood to offer distinct advantages over the current state of the relevant art. First, as already discussed above, the basic process methodology of the present invention enables the main body of a diaper to be fabricated of a rectangular configuration without cutting and discarding any waste material of the inner and outer webs, thereby accomplishing a significant cost savings over conventional methods wherein the discarded waste material represents as much as 11% of the overall material costs of diapers. Further, the formation of the main diaper body of a rectangular configuration conveniently enables multiple pluralities of diaper bodies to be fabricated in side-by-side relation from a single composite web, thereby at least doubling the overall output of a single diaper processing line. The attachment of the diaper tabs by a fin-type seal avoids the conventional necessity with traditional diapers of manipulating the tabs into such overlapping relation as part of the process of folding and packaging diapers, thereby more conveniently simplifying and facilitating the folding and packaging of the diapers of the present invention.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A method of making diapers substantially without producing discarded waste material, comprising the steps of:

providing a composite web of diaper main body material comprising a substantially liquid impervious outer layer, a substantially liquid pervious inner layer and an absorbent intermediate layer between the outer and inner layers, the composite web having a longitudinal extent of an indeterminate continuous length substantially intact and uncut with substantially parallel linear edge margins along opposite lateral sides thereof for substantially the entire length of the composite web, providing a single independent web of diaper tab material having a longitudinal extent of indeterminate continuous length, cutting the web of diaper tab material into discrete tab sections of predetermined mating shapes which produce substantially no waste material which is unused as the tab sections, placing each tab section in overlying relation to the composite web at predetermined regular longitudinal spacings along the composite web and with respective edges of the tab sections in alignment with the edge margins of the composite web without projection of the tab sections beyond the edge margins of the composite web, affixing the tab sections to the opposite edge margins of the composite web in said overlying relation by forming a seal between the respective aligned edges of each tab section and the edge margins of the composite web, cutting the composite web transversely at regular longitudinal intervals therealong corresponding to the spacings of the tab sections and including cutting of the tab sections into discrete tabs to produce a plurality of discrete diapers each having a generally rectangular main body and one tab at each respective corner of the main body substantially without cutting and discarding any material from the composite web or the tabs.

2. A method of making diapers substantially without producing discarded waste material according to claim 1, wherein the step of providing a composite web of diaper main body material comprises forming the composite web of diaper main body material by providing the outer and inner layers of coextensive indeterminate continuous lengths having corresponding substantially parallel linear longitudinal edges along opposite lateral sides thereof, and assembling the outer and inner layers coextensively in overlying relation with one another substantially without cutting and discarding any material from the inner and outer layers.

3. A method of making diapers substantially without producing discarded waste material according to claim 2, wherein the forming of the composite diaper main body material further comprises the step of inserting the absorbent layer between the inner and outer layers.

4. A method of making diapers substantially without producing discarded waste material according to claim 3, wherein the forming of the composite diaper main body material further comprises inserting the absorbent layer as discrete absorbent pads spaced longitudinally from one another, the tab sections being affixed to the composite web at the spacings intermediately of the absorbent pads and the transverse cutting of the composite web being performed at the spacings intermediately of the absorbent pads.

5. A method of making diapers substantially without producing discarded waste material according to claim 1, wherein the step of transversely cutting the composite web is performed at a location longitudinally intermediate along the tab sections for separating each tab section into at least two tabs.

6. A method of making diapers substantially without producing discarded waste material according to claim 1, further comprising the step of continuously advancing the composite web of diaper main body material and the independent web of diaper tab material in synchronism with respect to each other, said steps of cutting the web of diaper tab material, affixing the tab sections and cutting the composite web being performed during said advancing of the composite web of diaper main body material and the independent web of diaper tab material.

7. A method of making diapers substantially without producing discarded waste material, comprising the steps of:

forming a composite web of diaper main body material by providing a substantially liquid impervious outer layer and a substantially liquid pervious inner layer of coextensive indeterminate continuous lengths having corresponding substantially parallel linear longitudinal edges along opposite lateral sides thereof, inserting between the outer and inner layers an intermediate absorbent layer of a plurality of discrete absorbent pads arranged in two laterally spaced longitudinal rows of correspondingly longitudinally spaced absorbent pads, and assembling the outer and inner layers coextensively with one another substantially without cutting and discarding any material from the inner and outer layers thereby to form the composite web with a longitudinal extent of an indeterminate continuous length with substantially parallel linear edge margins along opposite lateral sides thereof for substantially the entire length of the composite web, providing a single independent web of diaper tab material having a longitudinal extent of indeterminate continuous length, cutting the web of tab material into a plurality of discrete tab sections of predetermined mating shapes which produce substantially no waste material which is unused as the tab sections, placing each tab section in overlying relation to the composite web at predetermined regular longitudinal spacings therealong corresponding to the spacings intermediately of the absorbent pads with one subplurality of the tab sections disposed intermediate the two laterally spaced longitudinal rows of absorbent pads and with a second subplurality of the tab sections disposed with respective edges thereof in alignment with the edge margins of the composite web without projection of the second tab sections beyond the edge margins of the composite web, and affixing the tab sections to the composite web in said overlying relation by forming a seal between the respective aligned edges of each second tab section and the opposite edge margins of the composite web and by forming a seal between each first tab section and the composite web longitudinally intermediate the longitudinal rows of the absorbent pads, and cutting the composite web longitudinally between the longitudinal rows of the absorbent pads transversely intermediate the tab sections therebetween and cutting the composite web transversely at regular longitudinal intervals at locations longitudinally intermediate along the tab sections, including cutting of the tab sections into discrete tabs, to produce two pluralities of discrete diapers substantially without cutting and discarding any material from the composite web or the tabs, each diaper having a generally rectangular main body and one tab at each respective corner of the main body.

8. A method of making diapers substantially without producing discarded waste material according to claim 7, further comprising the step of advancing the composite web of diaper main body material and the independent web of diaper tab material in synchronism with respect to each other, said steps of cutting the web of diaper tab material, affixing the tab sections and cutting the composite web being performed during said advancing of the composite web of diaper main body material and the independent web of diaper tab material.

* * * * *